US 8,748,997 B2

(12) United States Patent
Kim et al.

(10) Patent No.: US 8,748,997 B2
(45) Date of Patent: Jun. 10, 2014

(54) CONTACT-FORCE SENSOR PACKAGE AND METHOD OF FABRICATING THE SAME (75) Inventors: Jong-pal Kim, Yongin-si (KR); Byeung-leul Lee, Chungnam Province (KR)

(73) Assignees: Samsung Electronics Co., Ltd. (KR); Center for University-Industry Corporation (KR)

( * ) Notice: Subject to any disclaimer, the term of this patent is extended or adjusted under 35 U.S.C. 154(b) by 858 days.

(21) Appl. No.: 12/547,082

(22) Filed: Aug. 25, 2009

(65) Prior Publication Data
US 2010/0148286 A1 Jun. 17, 2010

(30) Foreign Application Priority Data

Dec. 16, 2008 (KR) .................. 10-2008-0128188

(51) Int. Cl.
*H01L 29/84* (2006.01)
(52) U.S. Cl.
USPC ........ 257/415; 257/417; 257/418; 340/407.1; 434/113
(58) Field of Classification Search
CPC ............. H01H 59/0009; H01H 1/0094; G01R 1/06727; G01R 1/07342; G01Q 60/38; G06F 3/016; G06F 3/041; G06F 3/03547; G06F 3/0414; G06F 3/0488
USPC ............... 257/252–254, 415–420; 340/407.1, 340/825.19; 434/112, 113
See application file for complete search history.

(56) References Cited

U.S. PATENT DOCUMENTS

| | | | |
|---|---|---|---|
| 3,624,315 A * | 11/1971 | Broce et al. ................... 369/134 |
| 4,409,983 A | 10/1983 | Albert | |
| 5,243,992 A | 9/1993 | Eckerle et al. | |
| 5,406,952 A | 4/1995 | Barnes et al. | |
| 6,210,340 B1 | 4/2001 | Amano et al. | |
| 6,445,284 B1 * | 9/2002 | Cruz-Hernandez et al. ........................ 340/407.1 |
| 2003/0212335 A1 | 11/2003 | Huang | |
| 2007/0211032 A1 * | 9/2007 | Ahn et al. ..................... 345/163 |
| 2008/0022513 A1 * | 1/2008 | Liu et al. ..................... 29/621.1 |
| 2008/0072682 A1 * | 3/2008 | Liu et al. ........................ 73/756 |

FOREIGN PATENT DOCUMENTS

| | | |
|---|---|---|
| JP | 2004-208711 | 7/2004 |
| JP | 2005-352739 | 12/2005 |
| JP | 2007-319343 | 12/2007 |
| KR | 1020050010396 A | 1/2005 |

OTHER PUBLICATIONS

Gary M. Drzewiecki et al., "Arterial Tonometry: Review and Analysis", J. Biomechanics, vol. 16, No. 2, 1983, pp. 141-152.

* cited by examiner

*Primary Examiner* — H Tsai
(74) *Attorney, Agent, or Firm* — Cantor Colburn LLP (57) ABSTRACT

Provided are a contact-force sensor package and a method of fabricating the same. The contact-force sensor package includes an elastic layer comprising a side that contacts a source of a contact-force; and a substrate layer adhered to the opposing side of the elastic layer from the side that contacts the source of the contact-force and comprising a cantilever beam separated from the elastic layer and deformed due to the contact-force, a pillar extending from a free end portion of the cantilever beam to the elastic layer and transferring the contact-force from the elastic layer to the cantilever beam, and a deformation sensing element for generating an electrical signal that is proportional to a degree of deformation of the cantilever beam.

9 Claims, 6 Drawing Sheets

CONTACT-FORCE SENSOR PACKAGE AND METHOD OF FABRICATING THE SAME

CROSS-REFERENCE TO RELATED APPLICATIONS

This application claims priority to Korean Patent Application No. 10-2008-0128188, filed on Dec. 16, 2008, and all the benefits accruing therefrom under 35 U.S.C. §119, the content of which in its entirety is herein incorporated by reference.

BACKGROUND

1. Field

Disclosed herein is a contact-force sensor package, which contacts a human body and senses a sphygmus wave so as to measure blood pressure. Disclosed herein too is a method of fabricating the contact-force sensor package.

2. Description of the Related Art

With the increase in people's awareness and concern about health, various methods of measuring blood pressure have been developed. Among methods of measuring blood pressure, a Korotkoff sounds method, an oscillometric method, and a tonometric method are often used. The Korotkoff sounds method is a traditional method of measuring blood pressure. According to the Korotkoff sounds method, when sufficient pressure is applied to a body part through which arterial blood flows, blood flow is blocked and then as the pressure applied to the body part is reduced, the pressure at which a pulse sound is first heard is measured as the systolic pressure, and the pressure at which the pulse sound disappears is measured as the diastolic pressure.

The oscillometric method and the tonometric method are applied to a digitized apparatus for measuring blood pressure. The oscillometric method measures the systolic pressure and the diastolic pressure by detecting a pulse wave generated in a depressurization process that depressurizes a body part at a constant speed. The detection of the pulse wave is conducted after sufficiently pressurizing the body part through which arterial blood flows so as to block arterial blood flow. This is similar to the Korotkoff sounds method. The oscillometric method may also be conducted in a pressurization process that pressurizes the body part at a constant speed. A pressure at which the amplitude of a pulse waveform is at a specific level may be measured as a function of the systolic pressure or the diastolic pressure, as compared with a pressure at which the amplitude of the pulse waveform is at a maximum. Alternatively, a pressure at which the amplitude of the pulse waveform varies greatly may be measured as a function of the systolic pressure or the diastolic pressure. During the depressurization process of the body part at a constant speed after the pressurization process, the systolic pressure is measured before the moment at which the amplitude of the pulse waveform is at the maximum, and the diastolic pressure is measured after the moment at which the amplitude of the pulse waveform is at the maximum. On the contrary, in the pressurization process of the body part at a constant speed, the systolic pressure is measured after the moment at which the amplitude of the pulse waveform is at the maximum, and the diastolic pressure is measured before the moment at which the amplitude of the pulse waveform is at the maximum.

According to the tonometric method, blood pressure can be measured continuously according to the magnitude and shape of the sphygmus wave that is generated when a predetermined pressure at which the blood flow in the artery is not completely blocked is applied to the body part.

In the tonometric method, a contact-force sensor package, which contacts the skin to sense vibration of the artery so as to measure blood pressure, is used. The contact-force sensor package may include a beam that vibrates due to the sphygmus wave. In order to measure distribution of pressure along the widthwise direction of the artery, the contact-force sensor package includes a plurality of beams arranged in a line. The plurality of beams are arranged in the widthwise direction of the beams.

In order to more accurately measure blood pressure, the contact-force sensor package should be disposed on the artery so that the widthwise direction of the beams is perpendicular to the lengthwise direction of the artery. However, during measurement, it is not easy to accurately align and place the contact-force sensor package on the skin. The contact-force sensor package is often placed on the skin in a state where relative alignment with respect to the artery is difficult to perform accurately. As such, the accuracy of measuring the blood pressure of a patient is reduced.

SUMMARY

Disclosed herein is a contact-force sensor package in which accuracy of measurement is enhanced when blood pressure is measured using a tonometric method. Disclosed herein too is a method of fabricating the same.

Additional aspects will be set forth in part in the description which follows and, in part, will be apparent from the description, or may be learned by practice of the invention.

To achieve the above and/or other aspects, one or more embodiments may include a contact-force sensor package, the contact-force sensor package including an elastic layer comprising a side that contacts a source of a contact-force; and a substrate layer adhered to the opposing side of the elastic layer to the side that contacts the source of the contact-force; the substrate layer comprising a cantilever beam separated from the elastic layer and deformed due to the contact-force, a pillar for extending from a free end portion of the cantilever beam to the elastic layer and transferring the contact-force from the elastic layer to the cantilever beam, and a deformation sensing element for generating an electrical signal that is proportional to a degree of deformation of the cantilever beams.

The substrate layer may further include a stopper for restricting excessive movement of the pillar in a planar direction of the substrate layer.

The substrate layer may include a plurality of cantilever beams, a plurality of pillars, and a plurality of deformation sensing elements, and the plurality of cantilever beams, the plurality of pillars, and the plurality of deformation sensing elements may be arranged in a line.

A cavity that is not adhered to the elastic layer may be formed in the substrate layer around the pillar so that movement of the pillar is not restricted due to the contact-force.

The contact-force sensor package may further include a base layer comprising a terminal transferring the electrical signal generated by the deformation sensing element and a cavity formed around the cantilever beam so as not to interfere with deformation of the cantilever beam, wherein the base layer is adhered to a different side from the side of the substrate layer adhered to the elastic layer.

The elastic layer may include silicone or polydimethylsiloxane ("PDMS").

The substrate layer may include silicon ("Si").

The deformation sensing element may include a piezoresistor layer formed at a fixed end portion of the cantilever beam.

A contact surface of the pillar that contacts the elastic layer may be a circle or a regular polygon.

To achieve the above and/or other aspects, one or more embodiments may include a method of fabricating a contact-force sensor package, the method including forming a cantilever beam at a side of a substrate layer, wherein the cantilever beam is deformed due to a contact-force; forming a deformation sensing element that generates an electrical signal that is proportional to a degree of deformation of the cantilever beam; etching a portion of the opposing side of the substrate layer to form a pillar connected to a free end portion of the cantilever beam; and adhering an elastic layer to the other side of the substrate layer.

The forming of the pillar may include forming an etch stopper comprising an exposure area in which an etch stopping material is not stacked, a first layer area in which the etch stopping material is stacked to a thickness of a first layer, and a second layer area in which the etch stopping material is stacked to a thickness of a second layer that is larger than the first layer, at the opposing side of the substrate layer; forming a groove by etching the substrate layer through the exposure area; removing the first area layer; and etching the substrate layer through the removed first area layer and the groove to form the pillar and a cavity around the pillar.

The method may further include adhering a base layer comprising a terminal for transferring the electrical signal generated by the deformation sensing element and a cavity formed around the cantilever beam so as not to interfere with deformation of the cantilever beam, to a side of the substrate layer.

The forming of the deformation sensing element may include forming a piezoresistor layer at a fixed end portion of the cantilever beam.

BRIEF DESCRIPTION OF THE DRAWINGS

The above and other aspects, advantages and features of this disclosure will become more apparent by describing in detail exemplary embodiments thereof with reference to the accompanying drawings, in which.

DETAILED DESCRIPTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Figure 1:
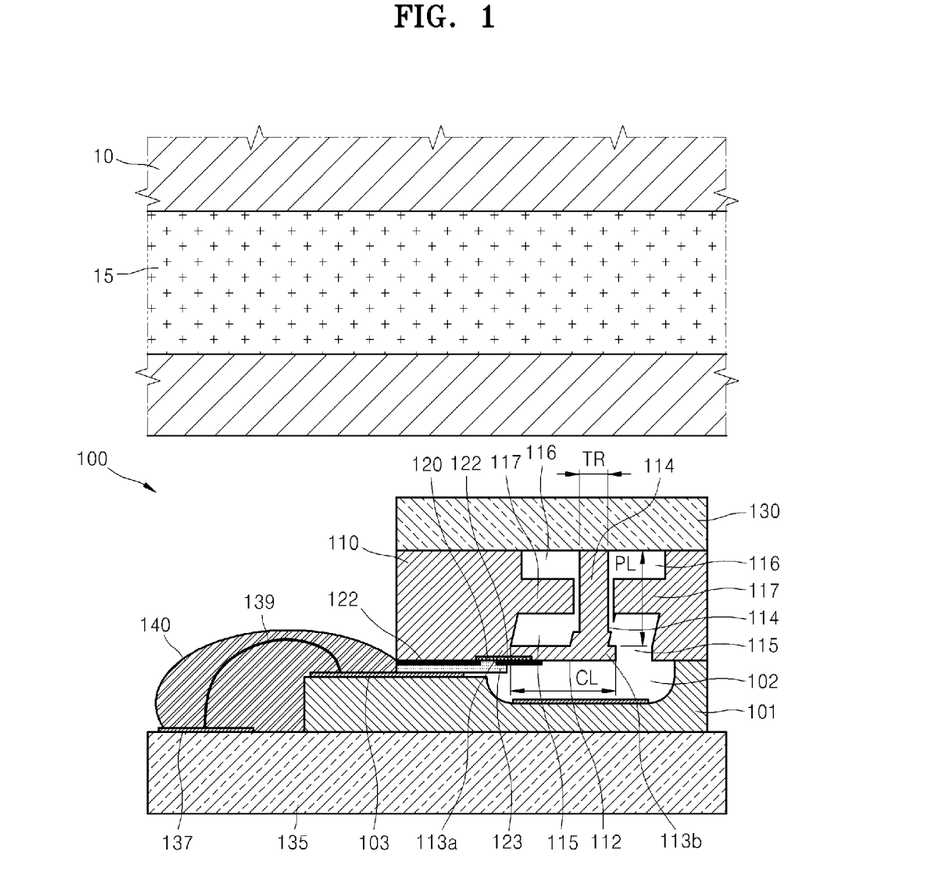
FIG. 1 is an exemplary longitudinal cross-sectional view of a contact-force sensor package.
Figure 2:
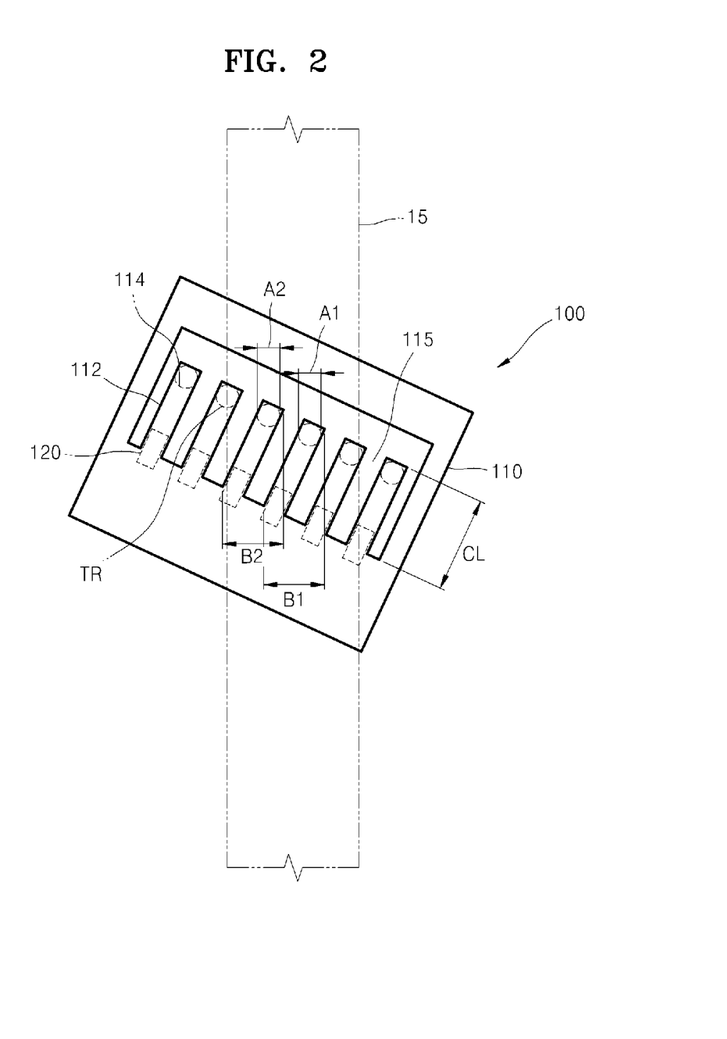
FIG. 2 is an exemplary plan view of a substrate layer of the contact-force sensor package illustrated in FIG. 1, which overlaps with the radial artery of a person who is to be examined when a blood pressure measuring device including the contact-force sensor package of FIG. 1 is placed around the wrist of the person to be examined.

FIG. 1 is an exemplary longitudinal cross-sectional view of a contact-force sensor package 100, and FIG. 2 is an exemplary plan view of a substrate layer of the contact-force sensor package 100 illustrated in FIG. 1, which overlaps with the radial artery 15 of a person who is to be examined. The person is examined by placing the blood pressure measuring device including the contact-force sensor package 100 of FIG. 1 on the wrist.

Referring to FIG. 1, the contact-force sensor package 100 is included in a portable blood pressure measuring device (not shown) placed around the wrist 10 and contacts the wrist 10 through which the radial artery 15 passes, to sense a sphygmus wave. The contact-force sensor package 100 includes a base layer 101, a substrate layer 110 adhered to a first side of the base layer 101, and an elastic layer 130, which is adhered to the substrate layer 110, contacts the skin of the person to be examined and is a source of a contact-force when blood pressure is measured. The elastic layer 130 may be formed by adhering a film formed of silicone or polydimethylsiloxane ("PDMS") to the substrate layer 110.

A material used in forming the substrate layer 110 may include silicon ("Si"). The substrate 110 includes a cantilever beam 112 separated from the elastic layer 130, a pillar 114 extending from the cantilever beam 112 to the elastic layer 130, and a deformation sensing element 120 for generating an electrical signal. The magnitude of the electrical signal is proportional to the degree of deformation of the cantilever beam 112. The substrate layer 110 including the cantilever beam 112, the pillar 114, and the deformation sensing element 120 may be formed by using processes similar to those use for fabricating a microelectromechanical system ("MEMS").

The cantilever beam 112 includes a fixed end portion 113a and a free end portion 113b. The pillar 114 extends from the free end portion 113b of the cantilever beam 112 to the elastic layer 130 and is adhered (e.g., fixedly attached) onto the elastic layer 130. The length PL of the pillar 114 corresponds to a distance at which the cantilever beam 112 and the elastic layer 130 are separated from each other. The length PL of the pillar 114 may be greater than the length CL of the cantilever beam 112. A contact surface TR of the pillar 114 that contacts the elastic layer 130 may be a circle or a regular polygon.

The deformation sensing element 120 is formed at the fixed end portion 113a of the cantilever beam 112 and may include a piezoresistor layer (not shown). When the cantilever beam 112 vibrates due to a contact-force that is transferred through the elastic layer 130 and the pillar 114 and is applied to the cantilever beam 112, an electrical resistance of the piezoresistor layer varies according to the degree of deformation of the cantilever beam 112. Thus, the sphygmus wave of the person to be examined can be measured by sensing changes in voltage by applying a predetermined current to the piezoresistor layer or by sensing changes in current by applying a predetermined voltage to the piezoresistor layer. As described above, the deformation sensing element 120 includes the piezoresistor layer but is not limited to the above described configuration. For example, the deformation sensing element 120 may include an element for sensing changes in piezoelectricity or capacitance that varies according to deformation of the cantilever beam 112.

A cavity 116 around the pillar 114 is intentionally cut out from a side of the substrate layer 110 adhered onto the elastic layer 130 and is formed therein so that a peripheral portion of the pillar 114 is not adhered to the elastic layer 130. If there is no cavity 116 and the pillar 114 and its peripheral portion are adhered to one elastic layer 130 then the reaction sensitivity of the pillar 114 and the cantilever beam 112 with respect to the contact-force may be reduced. Thus, in order to prevent this reduction in reaction sensitivity, the cavity 116 is disposed around the pillar 114. In addition, a cavity 115 around the cantilever beam 112 is formed in the other side of the substrate 110 adhered to the base layer 101. The cavity 115 around the cantilever beam 112 is formed to prevent lowering of the reaction sensitivity of the pillar 114 and the cantilever beam 112 with respect to the contact-force.

A stopper 117 is disposed between the cavity 116 around the pillar 114 and the cavity 115 around the cantilever beam 112 so as to restrict excessive movement of the pillar 114 in a planar direction of the substrate layer 110, i.e., to restrict excessive motion in a direction perpendicular to the lengthwise direction ("PL") of the pillar 114.

A material used in forming the base layer 101 may include glass. A cavity 102 is formed in a side of the base layer 101 that is adhered to the substrate layer 110 so as not to interfere with deformation of the cantilever beam 112 due to the contact-force. An insulator 122 is formed on the deformation sensing element 120 of the substrate layer 110 so that only a portion of the deformation sensing element 120 is exposed. A first terminal 123 is formed on the insulator 122 to be electrically connected to the deformation sensing element 120. A second terminal 103 is disposed on the base layer 101 and is directly bonded to the first terminal 123.

The contact-force sensor package 100 further includes a flexible printed circuit board ("FPCB") 135 on which the base layer 101, the substrate layer 110 and the elastic layer 130 are stacked. The FPCB 135 includes a third terminal 137 that is electrically connected to the second terminal 103 of the base layer 101 by using a bonding wire 139. The bonding wire 139 is protected due to a passivation layer 140 formed thereon.

Referring to FIG. 2, the substrate layer 110 of the contact-force sensor package 100 includes a plurality of cantilever beams 112, a plurality of pillars 114, and a plurality of deformation sensing elements 120. The plurality of cantilever beams 112, the plurality of pillars 114, and the plurality of deformation sensing elements 120 are arranged in a line in a direction perpendicular to the lengthwise direction of each of the cantilever beams 112 and perpendicular to the lengthwise direction of each of the pillars 114. When the contact-force sensor package 100 is placed over the radial artery 15 so as to measure blood pressure, at least two or more cantilever beams 112 of the plurality of cantilever beams 112 included in the substrate layer 110 are arranged in the widthwise direction of the radial artery 15. In one embodiment, when the contact-force sensor package 100 is placed over the radial artery 15 so as to measure blood pressure, at least two or more cantilever beams 112 of the plurality of cantilever beams 112 included in the substrate layer 110 are arranged so as to be inclined at an angle to a direction that is parallel to the direction of the length of the radial artery 15.

The contact-force of the radial artery 15 is transferred to each of the cantilever beams 112 only through the contact surface TR corresponding to the cantilever beams 112 and is measured by using each of the deformation sensing elements 120. Thus, even though the contact-force sensor package 100 is not well aligned on the radial artery 15 as shown in FIG. 2, an area used for measuring blood pressure does not overlap between the adjacent deformation sensing elements 120. For example, in a pair of adjacent cantilever beams 112 of FIG. 2, the contact surface TR of each of the pillars 114 that contacts the elastic layer 130 becomes the area required for measuring blood pressure. Thus, two adjacent areas A1 and A2 required for measuring blood pressure do not overlap with each other. Thus, accuracy of measuring blood pressure is enhanced.

If the cantilever beams 112 directly contact the elastic layer (see 130 of FIG. 1) without having to form the pillars 114, the areas of each of the deformation sensing elements 120, required for measuring blood pressure, become the entire bottom surface of each of the cantilever beams 112. Thus, when the contact-force sensor package 100 is not well aligned on the radial artery 15 as shown in FIG. 2, areas B1 and B2 of the adjacent, pair of cantilever beams 112, required for measuring blood pressure, overlap with each other. Thus, accuracy of measuring blood pressure over the width of the radial artery 15 may be lowered.

FIGS. 3A through 3G are longitudinal cross-sectional views illustrating a method of fabricating the contact-force sensor package 100 of FIG. 1. Hereinafter, the method of fabricating the contact-force sensor package 100 will be described with reference to FIGS. 3A through 3G.

Figure 3A:
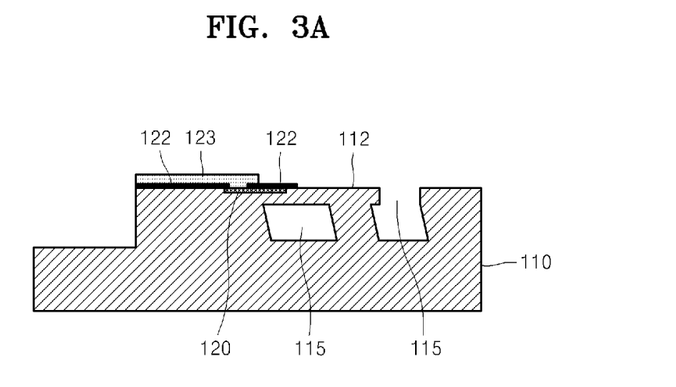
FIGS. 3A through 3G are longitudinal cross-sectional views illustrating a method of fabricating the contact-force sensor package of FIG. 1.

The method of fabricating the contact-force sensor package 100 of FIG. 1 includes forming the cantilever beam 112; forming the deformation sensing element 120; adhering the base layer 101; forming the pillar 114; and adhering the elastic layer 130. Referring to FIG. 3A, the forming of the cantilever beam 112 includes preparing the substrate layer 110 formed of silicon ("Si") and forming the cantilever beam 112 by etching a side of the substrate layer 110 in a predetermined pattern. As an example of an etching method, wet etching with relatively low costs may be used. Due to the etching, a portion of the substrate layer 110 is removed, thereby forming the cavity 115 around the cantilever beam 112.

The forming of the deformation sensing element 120 may include forming a piezoresistor layer by using ion implantion. Only a portion of the deformation sensing element 120 is exposed and the deformation sensing element 120 is covered by the insulator 122, and the first terminal 123 formed of metal is formed on the insulator 122. As such, the deformation sensing element 120 and the first terminal 123 are electrically connected to each other.

Figure 3B:
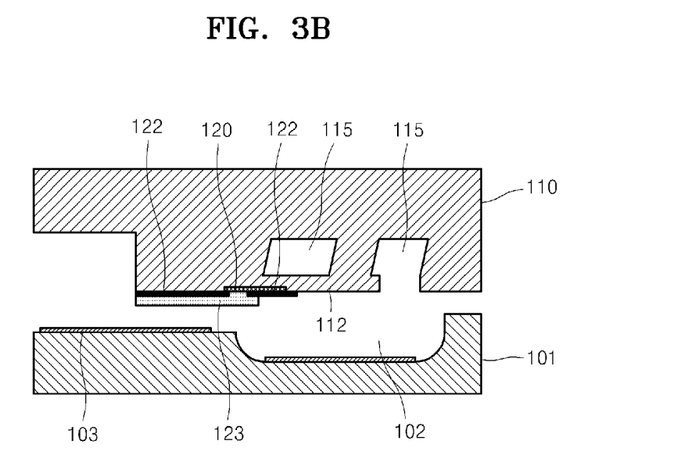

Referring to FIG. 3B, the adhering of the base layer 101 includes preparing the base layer 101 formed of glass; forming the cavity 102 in a side of the base layer 101 that is not adhered to the substrate layer 110 so as not to interfere with deformation of the cantilever beam 112 due to the contact-force; forming the second terminal 103 formed of metal at a position where the second terminal 103 overlaps with the first terminal 123; and bonding a side of the substrate layer 110 in which the deformation sensing element 120 is formed, to a side of the base layer 101 in which the second terminal 103 is formed. The substrate layer 110 and the base layer 101 may be bonded to each other by applying an adhesive or by anodic bonding.

Figure 3C:
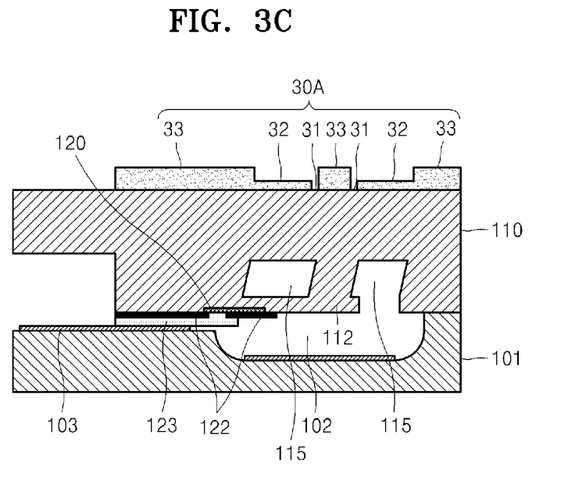

Referring to FIG. 3C, the forming of the pillar (see 114 of FIG. 1) includes forming an etch stopper 30A including an exposure area 31 in which an etch stopping material is not stacked on the opposite side to the side of the substrate layer 110 bonded to the base layer 101, a first layer area 32 in which the etch stopping material is stacked to a thickness of a first layer, and a second layer area 33 in which the etch stopping material is stacked to a thickness of a second layer that is larger than the first layer. The etch stopping material may include plasma-enhanced chemical vapor deposition ("PECVD") oxide or PECVD nitride.

In order to stack etch stopping materials having different thicknesses, the etch stopping materials are, for example, deposited to the same thickness as that of the second layer area 33. Then, the etch stopping materials are removed from the remaining portions excluding the second layer area 33 to a predetermined thickness by using a first mask (not shown) that shields the second layer area 33 only, and is formed to the same thickness as that of the first layer area 32. Next, all of the etch stopping materials are removed from the remaining portions excluding the first layer area 32 and the second layer area 33 by using a second mask (not shown) that shields the first layer area 32 and the second layer area 33. The shape of the exposure area 31 corresponds to the shape of the contact surface TR of the pillar (see 114 of FIG. 1). The shape of the first layer area 32 corresponds to the shape of the cavity 116 around the pillar (see 114 of FIG. 1).

Figure 3D:
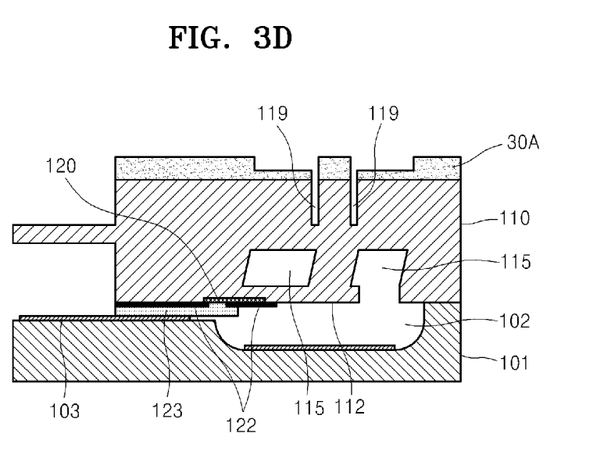

Referring to FIG. 3D, the forming of the pillar (see 114 of FIG. 1) includes forming a groove 119 by etching the substrate layer 110 through the exposure area 31. In the etching of the exposure area 31, a narrow area thereof is etched to a relatively large depth and thus, dry etching may be used. The etch process may be referred to as first etching for forming the pillar 114. In the first etching, the substrate layer 110 is etched to only half the depth to be etched, so as to form the pillar 114.

Figure 3E:
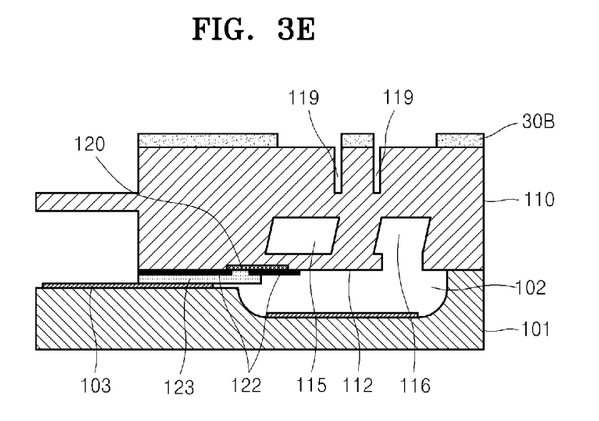

Referring to FIG. 3E, the forming of the pillar 114 includes removing the first layer area (see 32 of FIG. 3C) to expose the substrate layer 110 corresponding to the first layer area (see 32 of FIG. 3C). The etch stopper 30A having the thickness of the second layer is dry etched to a thickness of the etch stopping material of the first layer area (see 32 of FIG. 3C), thereby etching the substrate layer 110 corresponding to the first layer area (see 32 of FIG. 3C). An etch stopper 30B is deformed so that only a portion of the etch stopper 30B corresponding to the second layer area (see 33 of FIG. 3C) remains, and the thickness of the etch stopper 30B is reduced.

Figure 3F:
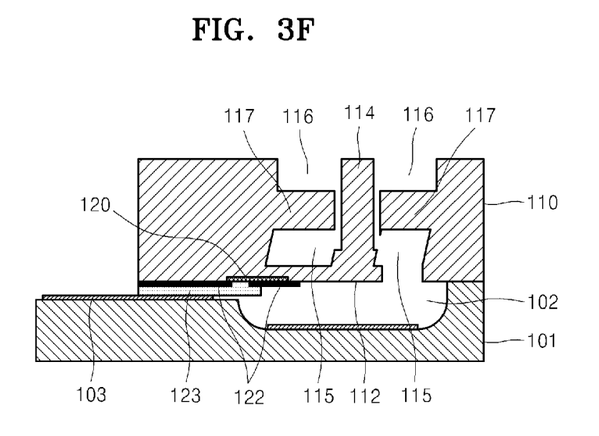

Referring to FIG. 3F, the forming of the pillar 114 further includes forming the cavity 116 around the pillar 114 by etching the substrate 110 through an area exposed through the etch stopper 30B, i.e., the groove (see 119 of FIG. 3E) and the first layer area (see 32 of FIG. 3C). The etching process may be referred to as a second etching for forming the pillar 114. Since the second etching includes etching the groove 119, which is a narrow area to a relatively large depth, dry etching may be used. After the pillar 114 is formed, the etch stopper 30B is removed. By performing the second etching, the stopper 117 is disposed between the cavity 116 around the pillar 114 and the cavity 115 around the cantilever beam 112.

Figure 3G:
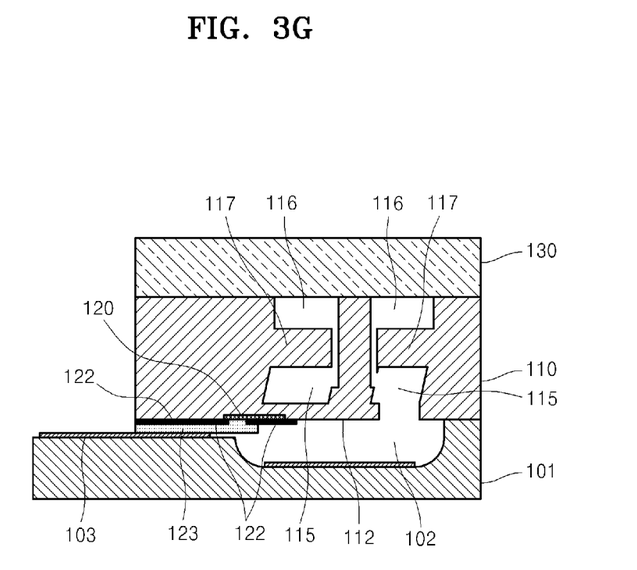

Referring to FIG. 3G, the adhering of the elastic layer 130 includes adhering the film-shaped elastic layer 130 to the substrate layer 110. A MEMS shown in FIG. 3G is placed on the FPCB (see 135 of FIG. 1), and the second terminal 103 and the third terminal (see 137 of FIG. 1) are electrically connected to each other by using the bonding wire (see 139 of FIG. 1), and the passivation layer (see 140 of FIG. 1) is formed to protect the bonding wire 139, thereby fabricating the contact-force sensor package (see 100 of FIG. 1).

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A contact-force sensor package comprising:
an elastic layer comprising a side that contacts a source of a contact-force; and
a substrate layer adhered to the opposing side of the elastic layer to the side that contacts the source of the contact-force, wherein a cavity that is not adhered to the elastic layer is formed in the substrate layer; the substrate layer further comprising:
a cantilever beam disposed in the cavity, separated from the elastic layer and deformed due to the contact-force;
a pillar extending from a free end portion of the cantilever beam to the elastic layer and transferring the contact-force from the elastic layer to the cantilever beam; where the substrate layer, the cantilever beam and the pillar are a single unitary piece; and
a deformation sensing element for generating an electrical signal that is proportional to a degree of deformation of the cantilever beams;
wherein an end portion of the pillar contacts a side of the elastic layer that is opposed to the side that contacts a source of a contact-force.

2. The contact-force sensor package of claim 1, wherein the substrate layer further comprises a stopper for restricting excessive movement of the pillar in a planar direction of the substrate layer.

3. The contact-force sensor package of claim 1, wherein the substrate layer further comprises a plurality of cantilever beams, a plurality of pillars, and a plurality of deformation sensing elements, and the plurality of cantilever beams, the plurality of pillars, and the plurality of deformation sensing elements are arranged in a line.

4. The contact-force sensor package of claim 1, wherein the cavity is formed in the substrate layer around the pillar so that movement of the pillar is not restricted due to the contact-force.

5. The contact-force sensor package of claim 1, further comprising a base layer comprising a terminal for transferring the electrical signal generated by the deformation sensing element and a cavity formed around the cantilever beam so as not to interfere with deformation of the cantilever beam, wherein the base layer is adhered to a different side from the side of the substrate layer adhered to the elastic layer.

6. The contact-force sensor package of claim 1, wherein the elastic layer comprises silicone or polydimethylsiloxane.

7. The contact-force sensor package of claim 1, wherein the substrate layer comprises silicon.

8. The contact-force sensor package of claim 1, wherein the deformation sensing element comprises a piezoresistor layer formed at a fixed end portion of the cantilever beam.

9. The contact-force sensor package of claim 1, wherein a contact surface of the pillar that contacts the elastic layer is a circle or a regular polygon.

* * * * *